US010772993B2

(12) United States Patent
Raina et al.

(10) Patent No.: US 10,772,993 B2
(45) Date of Patent: Sep. 15, 2020

(54) DRUG COATED MEDICAL DEVICES

(71) Applicant: Medtronic Vascular Inc., Santa Rosa, CA (US)

(72) Inventors: Shashank Raina, San Rafael, CA (US); John Kantor, Healdsburg, CA (US); Susan Peterson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 192 days.

(21) Appl. No.: 15/901,711

(22) Filed: Feb. 21, 2018

(65) Prior Publication Data

US 2018/0236139 A1 Aug. 23, 2018

Related U.S. Application Data

(60) Provisional application No. 62/462,399, filed on Feb. 23, 2017.

(51) Int. Cl.
| | |
|---|---|
| *A61L 29/08* | (2006.01) |
| *A61L 31/10* | (2006.01) |
| *A61L 31/16* | (2006.01) |
| *A61L 29/16* | (2006.01) |
| *A61K 31/337* | (2006.01) |
| *A61M 25/10* | (2013.01) |
| *A61K 47/69* | (2017.01) |
| *A61L 29/06* | (2006.01) |
| *A61P 9/10* | (2006.01) |
| *A61L 31/06* | (2006.01) |
| *A61F 2/82* | (2013.01) |

(52) U.S. Cl.
CPC .......... *A61L 29/085* (2013.01); *A61K 31/337* (2013.01); *A61K 47/6931* (2017.08); *A61L 29/06* (2013.01); *A61L 29/16* (2013.01); *A61L 31/06* (2013.01); *A61L 31/10* (2013.01); *A61L 31/16* (2013.01); *A61M 25/104* (2013.01); *A61P 9/10* (2018.01); *A61F 2/82* (2013.01); *A61F 2250/0067* (2013.01); *A61L 2300/416* (2013.01); *A61L 2300/602* (2013.01); *A61L 2300/606* (2013.01); *A61L 2300/80* (2013.01); *A61L 2400/12* (2013.01); *A61L 2400/18* (2013.01); *A61M 2025/105* (2013.01)

(58) Field of Classification Search
CPC ..... A61F 2/82; A61K 47/6931; A61M 25/104
See application file for complete search history.

(56) References Cited

U.S. PATENT DOCUMENTS

| | | | |
|---|---|---|---|
| 2005/0287184 A1* | 12/2005 | Hossainy | A61L 31/10 |
| | | | 424/423 |
| 2006/0095122 A1 | 5/2006 | Pacetti | |
| 2006/0188543 A1 | 8/2006 | Feng | |
| 2007/0148251 A1 | 6/2007 | Hossainy et al. | |
| 2013/0284310 A1 | 10/2013 | Peterson et al. | |
| 2016/0296631 A1 | 10/2016 | Johnson et al. | |
| 2017/0072116 A1* | 3/2017 | Antoni | A61L 27/28 |

FOREIGN PATENT DOCUMENTS

| | | |
|---|---|---|
| CN | 102274553 A | 12/2011 |
| DE | 202013002567 U1 | 6/2013 |
| WO | WO-2018106738 A1 * 6/2018 | ............. A61K 47/60 |

OTHER PUBLICATIONS

Database WPI, Section CH, Week 201204, Thomson Scientific, London, GB, Class A96, AN 2012-A22529, He et al,. "Coronary Artery Bracket, has bracket body coated with hyper-branched star amphiphilic SPLA-b-PMPC type polymer nano-particle," 1 page.
European Search Report, EP Patent Application No. 18158395.6, dated Jul. 2, 2018, 11 pages.
Liu, "Design and Development of Brush-Arm Star Polymers for Applications in Drug Delivery," Doctoral Thesis, Massachusetts Institute of Technology, Feb. 2017, 227 pages.
Su et al., "Drug Delivery Strategies Employing Angioplasty Balloons for Treatment of Atherosclerosis," Abstract 18836, Circulation, 2013, 128:A18836.
Xiong et al., "Materials Technology in Drug Eluting Balloons: Current and Future Perspectives," *Journal of Controlled Release*, 2016; 239:92-106.
Liao, et al., "A Convergent Synthetic Platform for Single-Nanoparticle Combination Cancer Therapy: Ratiometric Loading and Controlled Release of Cisplatin, Doxorubicin, and Camptothecin," *J Am Chem Soc*, 2014; 136:5896-5899.
Liu et al., "'Brush-First' Method for the Parallel Synthesis of Photocleavable, Nitroxide-Labeled Poly(ethylene glycol) Star Polymers," *J Am Chem Soc*, 2012; 134:16337-16344.

* cited by examiner

Primary Examiner — Kyle A Purdy (57) ABSTRACT

A medical device includes a body defining an exterior surface, and a coating including a therapeutic agent-containing nanoparticle disposed on the exterior surface of the medical device. The nanoparticle may include a brush-arm star polymer. The therapeutic agent may be paclitaxel.

20 Claims, 8 Drawing Sheets

DRUG COATED MEDICAL DEVICES

RELATED APPLICATIONS

This application claims the benefit of U.S. Provisional Patent Application 62/462,399 filed Feb. 23, 2017. The disclosure of which is herein incorporated by reference in its entirety.

FIELD

The present disclosure relates to, among other things, medical devices such as inflatable balloon catheters; and more particularly to drug-coated medical devices.

TECHNICAL BACKGROUND

Vascular atherosclerotic lesions that create arterial luminal narrowing are typically treated in angioplasty procedures via catheters provided with an inflatable balloon. The catheter is advanced, typically following a guidewire, to an opening within the atherosclerotic lesion of the narrowed artery. Once the inflatable balloon has been arranged at the artery narrowing, it may be inflated and deflated, sometimes repeatedly. The inflation, with successive deflation, of the inflatable balloon within the artery can reduce the extent of the arterial luminal narrowing, and restore a suitable blood flow.

In many cases, patients develop a re-narrowing of the vessel lumen at the intervention point within a few months. Such re-narrowing, or restenosis, is due to a cell hyperproliferation process, particularly of the vascular smooth muscle cells, and may be due to the dilating action caused by the inflatable balloon.

Inflatable balloons or stents can be coated with a drug having anti-proliferative action to prevent or retard restenosis. Among the drugs usually employed to such aim, paclitaxel (taxol) has proved to be particularly efficient.

However, with current therapies the paclitaxel delivered by the balloon catheter to the wall of the vessel drops below an effective concentration after a period of time. For example, the paclitaxel may be present on the vessel wall in an effective anti-proliferative concentration for about 6 months following treatment. It may be desirable to increase the amount of time that paclitaxel is present at the vessel wall in an effective concentration.

BRIEF SUMMARY

Described herein, among other things, is a medical device on which a coating comprising at least one nanoparticle containing a therapeutic agent is disposed. The medical device is configured to deliver the nanoparticle to a wall of a vessel of the patient. For example, the medical device may comprise a coated balloon that when inflated in a vessel of a patient may deliver the nanoparticles to the wall of the vessel. The therapeutic agent may be released from the nanoparticles over time. Accordingly, the use of nanoparticles as described herein may prolong the duration over which the therapeutic agent is present in the vessel wall at an effective concentration relative to medical devices coated with the therapeutic agent without the nanoparticle.

The nanoparticle-coated medical devices described herein may provide suitable vehicles for delivering more than one therapeutic agent to the wall of a vessel. The therapeutic agents may be selected to prevent restenosis through a variety of mechanisms of action to enhance the chance of successful and durable treatment. In some embodiments, different agents may be released at different times so the therapeutic agents may be present in effective concentrations at appropriate times to act on different biological factors released during the restenosis cascade.

The nanoparticle-coated medical devices described herein may provide suitable vehicles for delivering therapeutic agents that have short in vivo half-lives. The nanoparticles may effectively extend the half-life of the therapeutic agents. In some embodiments, therapeutic agents that would not have previously been used to treat a wall of a vessel due to their short half-life may be effectively used due to the protective effects of the nanoparticle.

The nanoparticle-coated medical devices described herein may provide suitable vehicles for delivering therapeutic agents that have narrow therapeutic indices (agents whose effective therapeutic concentrations are close to their toxic concentrations). The nanoparticles may control the release rate of such therapeutic agents to maintain therapeutic concentrations and avoid toxic levels. Such therapeutic agents may not have previously been useful for coating on a medical device for which the release of the agent may result in doses above a toxicity level.

The nanoparticles may release therapeutic agent following delivery to a wall of a vessel over time, in response to a stimuli, or both with the passage of time and in response to a stimuli.

In one aspect, the present disclosure describes a medical device comprising a body having an exterior surface. A coating is disposed on an exterior surface of the medical device. The coating comprises a nanoparticle containing a therapeutic agent. The nanoparticle may comprise a brush-arm star polymer. The medical device may comprise, for example, an inflatable balloon or a stent on which the coating is disposed.

In another aspect, the present disclosure described a method for delivering a therapeutic agent to a tissue of a patient through the use of a medical device coated with a coating comprising a nanoparticle containing a therapeutic agent. The method includes delivering a coated portion of the device to a target location of the patient, then contacting the coated portion of the device to tissue at the target location to transfer the nanoparticle containing the therapeutic agent to the tissue. The therapeutic agent may be released from the nanoparticle at the tissue, for example, over time or in response to a stimulus.

In another aspect, the present disclosure describes a medical device including an inflatable balloon defining an interior surface and an exterior surface. The interior surface defines an interior space. A coating is disposed on an exterior surface of the balloon. The coating comprises a nanoparticle containing a therapeutic agent. The nanoparticle may comprise a brush-arm star polymer.

In yet another aspect, the present disclosure described a method for delivering a therapeutic agent to a tissue of a patient through the use of a medical device having an inflatable balloon coated with a coating comprising a nanoparticle containing a therapeutic agent. The method includes delivering the inflatable balloon of the device to a target location of the patient, then inflating the inflatable balloon by introducing a fluid into an interior space of the inflatable balloon to cause the coating to contact tissue at the target location. Inflating the balloon causes the balloon to expand against tissue of the patient to transfer the nanoparticle containing the therapeutic agent to the tissue. The therapeutic agent may be released from the nanoparticle at the tissue, for example, over time or in response to a stimulus.

In some embodiments described herein, a method for coating a medical device comprises applying a coating to an exterior surface of the device. The coating comprises a nanoparticle containing a therapeutic agent. The nanoparticle may comprise a brush-arm star polymer.

Advantages and additional features of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, in which.

The schematic drawings are not necessarily to scale.

DETAILED DESCRIPTION

Reference will now be made in greater detail to various embodiments of the subject matter of the present disclosure, some embodiments of which are illustrated in the accompanying drawings. Like numbers used in the figures refer to like components and steps. However, it will be understood that the use of a number to refer to a component in a given figure is not intended to limit the component in another figure labeled with the same number. In addition, the use of different numbers to refer to components in different figures is not intended to indicate that the different numbered components cannot be the same or similar to other numbered components.

The present disclosure describes, among other things, a medical device on which a coating comprising a nanoparticle containing a therapeutic agent is disposed. The nanoparticle is configured to control the release of the therapeutic agent, for example, during a desired time or in response to a desired stimulus.

The medical device may be coated with one or more nanoparticles that contain one or more therapeutic agents and, optionally, one or more therapeutic agents that are not included in nanoparticles to achieve a desired tissue concentration of therapeutic agent. The timing of the release of therapeutic agent, as well as the therapeutic agents used, may be tailored to treatment of a particular disease, such as restenosis.

Figure 1:
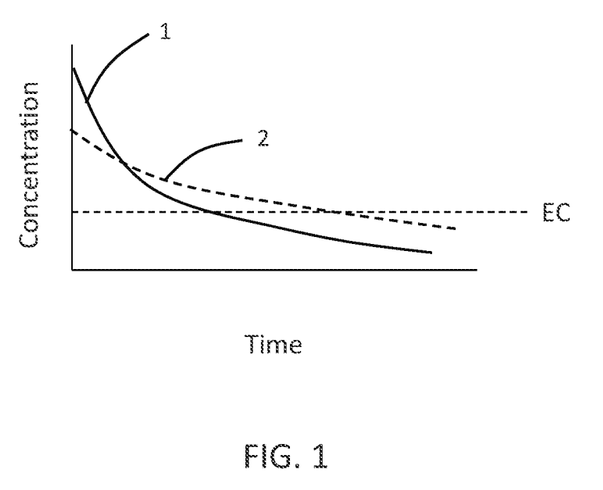
FIGS. 1-4 present examples of tissue concentration profiles of therapeutic agents that may be achieved by various embodiments of coated balloon catheters described herein.

FIGS. 1-4 present non-limiting examples of concentration profiles of therapeutic agents that may be desired following delivery by medical devices as described herein. For example, FIG. 1 schematically shows a tissue concentration profile of a therapeutic agent 1 that is not associated with a nanoparticle and a tissue concentration profile of a therapeutic agent 2 released from a nanoparticle. In the embodiment depicted in FIG. 1, the nanoparticle provides slow release rate of therapeutic agent. Accordingly, the initial concentration of therapeutic agent available to the tissue may be lower than with the therapeutic agent that is not associated with a nanoparticle. However, the therapeutic agent in the nanoparticle may remain at effective concentrations for longer than the therapeutic agent that is not associated with a nanoparticle. For purposes of illustration, a line (EC) that may be indicative of an effective concentration is shown.

Figure 2:
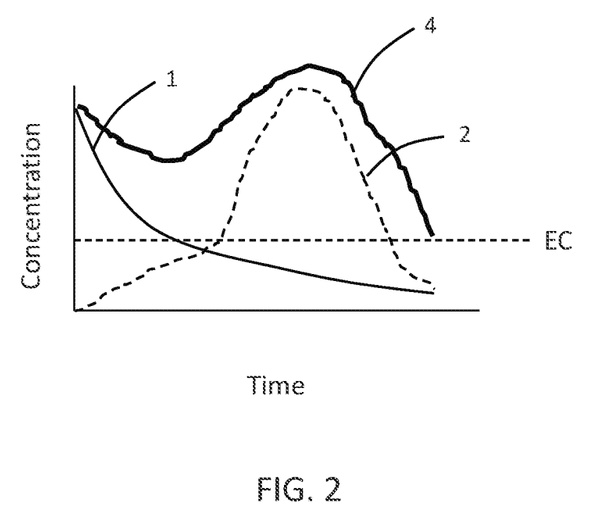

Referring now to FIG. 2, tissue concentration profile 1 of a therapeutic agent that is not associated with a nanoparticle and a tissue concentration profile 2 of a therapeutic agent released from a nanoparticle are schematically shown. In the depicted embodiment, the therapeutic agent released from the nanoparticle (trace 2) and the therapeutic agent not associated with the nanoparticle (trace 1) are the same and may be coated on the same balloon. In the depicted embodiment, the cumulative dose of therapeutic agent (sum of available therapeutic agent associated with nanoparticle and not associated with nanoparticle) is shown by schematic trace 4. In the depicted embodiment, release of the therapeutic agent from the nanoparticle is delayed. Preferably, substantial release of the therapeutic agent is delayed until the therapeutic agent not associated with the nanoparticle approaches concentrations that are near the effective concentration (illustrated by line EC). In the embodiment depicted in FIG. 2, effective concentrations of therapeutic agent may be maintained in the tissue for a substantially longer time than with the use of therapeutic agent not associated with nanoparticle alone. Compare schematic trace 1 (no nanoparticle) to schematic trace 4 (cumulative).

Figure 3:
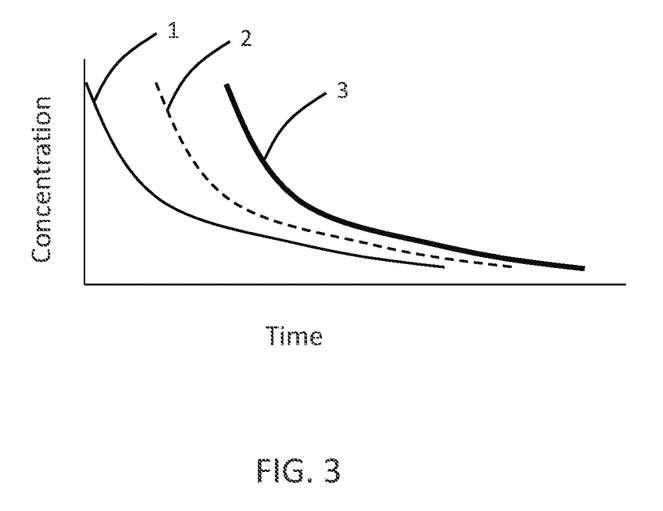

Referring now to FIG. 3, a schematic representation of tissue concentrations of therapeutic agents released from three different nanoparticles (1, 2, 3) is shown. The nanoparticles release therapeutic agents at different times, for example in response to a stimulus, such as light, a magnetic field, or the like. The three different nanoparticles may contain the same or different therapeutic agents.

Figure 4:
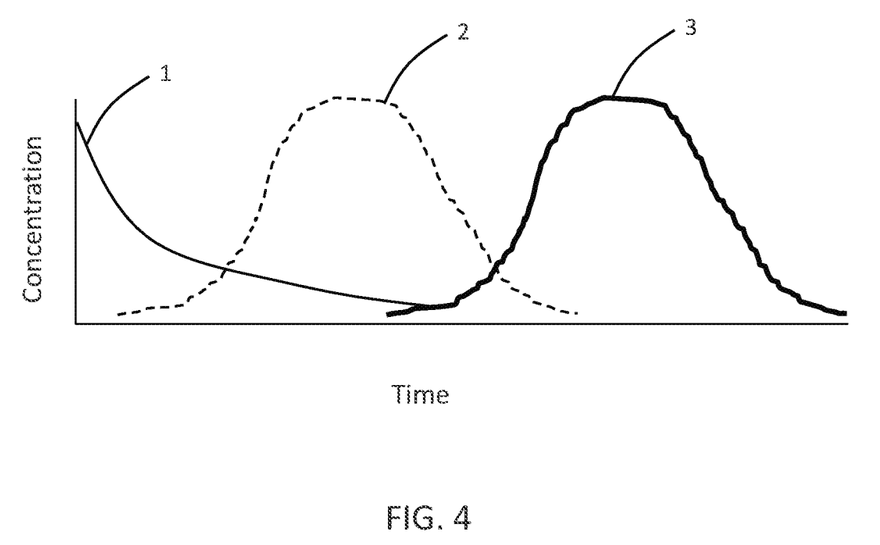

Referring now to FIG. 4, another schematic representation of tissue concentrations of therapeutic agents released from different nanoparticles is shown is shown. The schematic tissue concentration profile shown in trace 1 may be of a therapeutic agent associated with a nanoparticle or not associated with a nanoparticle. The schematic tissue concentration profile shown in trace 2 is of a therapeutic agent associated with a nanoparticle configured to delay the release of the therapeutic agent. The schematic tissue concentration profile shown in trace 3 is of a therapeutic agent associated with a nanoparticle configured to delay the release of the therapeutic agent even longer than the nanoparticle associated with trace 2. The therapeutic agent in the three traces (1, 2, 3) may be the same or different. If the therapeutic agent is the same, the effective concentration may be maintained for extended times. If the therapeutic agents are different, release is preferably timed to be most effective for the particular agent in light of the disease being treated.

Any suitable nanoparticle may be employed to control the timing of the release of the therapeutic agent. In some embodiments, the nanoparticle is configured to slowly release therapeutic agent contained in the nanoparticle over time following delivery of the nanoparticle to tissue of a patient. In some embodiments, the nanoparticle is configured to delay release of therapeutic agent after delivery to a tissue of a patient and then to release the agent slowly over time or in a more quick burst-like manner. In some embodiments, the nanoparticle is configured to release therapeutic agent upon exposure to a stimulus, such as light, an electromagnetic field, heat or the like. Once exposed to the stimulus the nanoparticle may be configured to release therapeutic agent rapidly, slowly or at a moderate rate.

More than one nanoparticle having one or more of the release properties described above may be employed to coat a medical device. One or more therapeutic agents may be incorporated into one or more of the nanoparticles. Accordingly, temporally controlled release of therapeutic agent following delivery of the nanoparticles to tissue of a patient, such as to a wall of a vessel to treat a stenosis and prevent restenosis, may be achieved.

In some embodiments, the nanoparticle comprises a brush-arm star polymer. Brush-arm star polymers are described in, for example, Lui et al., J. Am. Chem. Soc. 2012, 134, 16337-16344; Liao et al., J. Am. Chem. Soc. 2014, 136, 5896-5899; and U.S. Patent Application Publication No. 2016/0296631, each of which is hereby incorporated herein by reference in their entireties. One or more therapeutic agent may be attached to a component of the brush-arm star polymer.

A brush-arm star polymer may be prepared in any suitable manner. For example, a brush-arm star polymer may be prepared by polymerizing macro-monomers. As used herein, a "macro-monomer" is a macromolecule having a group that enables it to act as a monomer. Preferably, the polymerized macromolecules form a bottle-brush polymer having a living chain end. A plurality of bottle-brush polymer having a living chain ends may be connected by cross-linkers to a brush-arm star polymer. Such arm-first polymerization may enable synthesis of star polymers having moieties that are incompatible with radical polymerization. See, for example, Lui et al., J. Am. Chem. Soc. 2012, 134, 16337-16344.

Figure 5:
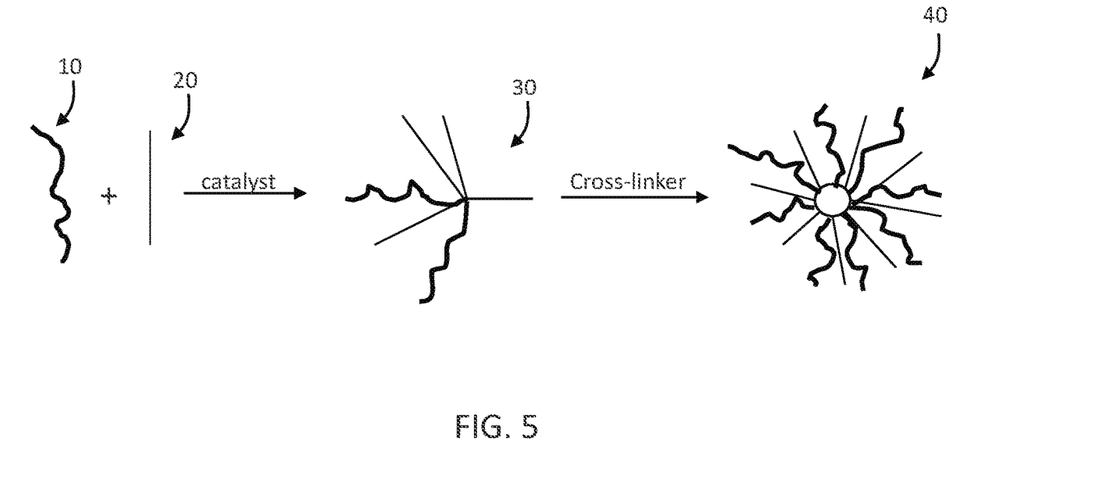
FIG. 5 is a general reaction scheme for producing a brush-arm star polymer in accordance with various embodiments described herein.

Referring now to FIG. 5, one or more macro-monomers 10, 20 may be polymerized in the presence of a catalyst to produce a bottle-brush polymer having a living chain ends 30. Multiple bottle-brush polymers having living chain ends 30 may be connected with one or more cross-linkers to form a brush-arm star polymer 40.

Figure 6:
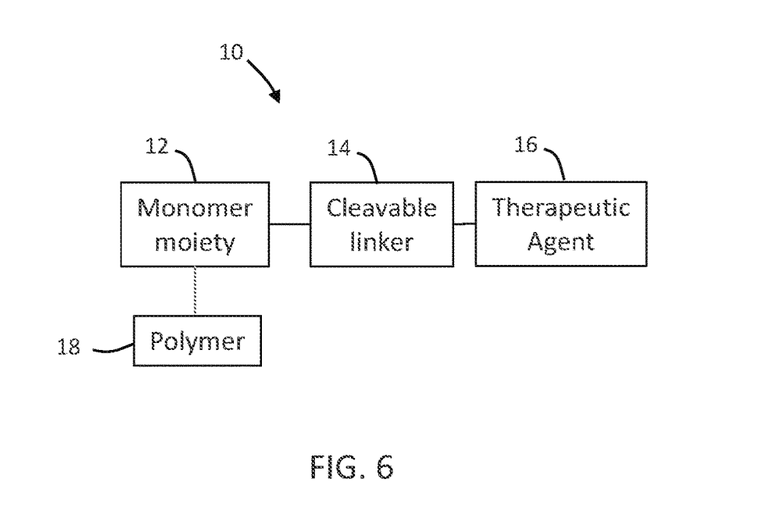
FIGS. 6-7 are schematic drawings of macro-monomers that may be used to form brush-arm star polymers in accordance with various embodiments described herein.

Referring now to FIG. 6, a schematic example of a macro-monomer 10 that may be employed to form a brush-arm star polymer is shown. The macro-monomer 10 may include a monomer moiety 12 and a cleavable linker 14 attaching a therapeutic agent 16 to the monomer moiety 12. The macro-monomer 10 may also include one or more polymers 18 attached to the monomer moiety 12; e.g., via a linker (not shown).

Figure 7:
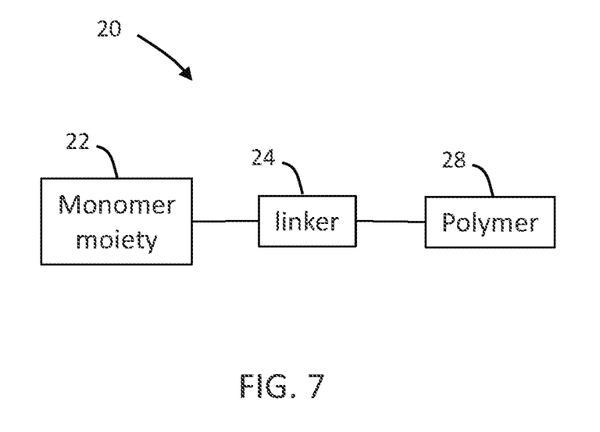

Referring now to FIG. 7, a schematic example of another macro-monomer 20 that may be employed to form a brush-arm star polymer is shown. The macro-monomer 20 may include a monomer moiety 22 and a linker 24, which may optionally be a cleavable linker, attaching a polymer 28 to the monomer moiety 22.

Figure 8:
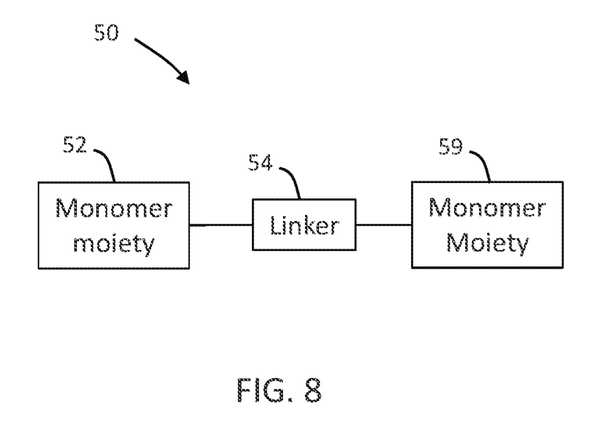
FIG. 8 is a schematic drawing of a cross-linker that may be used to form brush-arm star polymers in accordance with various embodiments described herein.

Referring now to FIG. 8, a schematic example of a cross-linker 50 that may be employed to form a brush-arm star polymer is shown. The cross-linker 50 comprises two or more monomer moieties 52, 59 joined by a linker 54, which may optionally be a cleavable linker.

The macro-monomers 10, 20 and the cross-linker 50 may, independently, include any suitable monomer moiety 12, 22, 52, 59. In some embodiments, the monomer moiety 12, 22, 52, 59 comprises a monomer moiety capable of being polymerized via ring-opening metathesis polymerization. For example, the monomer moiety 12, 22, 52, 59 may comprise a norbornene moiety.

Preferably, the polymers 18, 28 of the macro-monomers 10, 20 are hydrophilic. In some embodiments, the polymers 18, 28 comprise polyethylene glycol (PEG).

The cleavable linker 14 of the macro-monomer 10 may be any suitable cleavable linker. Upon cleavage of the cleavable linker 14, the therapeutic agent 16 may be released to act on tissue. For example, the cleavable linker 14 may be a linker cleaved by hydrolysis (such as an ester linkage), a photo-cleavable linker, a temperature sensitive linker, a magnetic field-induced cleavable linker, or the like. The cleavable linkers 14 cleavable by hydrolysis may cleave over time when exposed to bodily fluids, such as when delivered to a tissue of a patient. Light, heat, magnetic fields, or the like may be applied within the body or external to the body to cleave the linker. If the stimulus is applied external to the body, a sufficient amount of energy from the stimulus to cleave the linker should reach the location in which the nanoparticle is delivered.

Other linkers 24, 54 may, or may not, be cleavable. Preferably, the linker 54 of the cross-linker 50 is cleavable.

Figure 9:
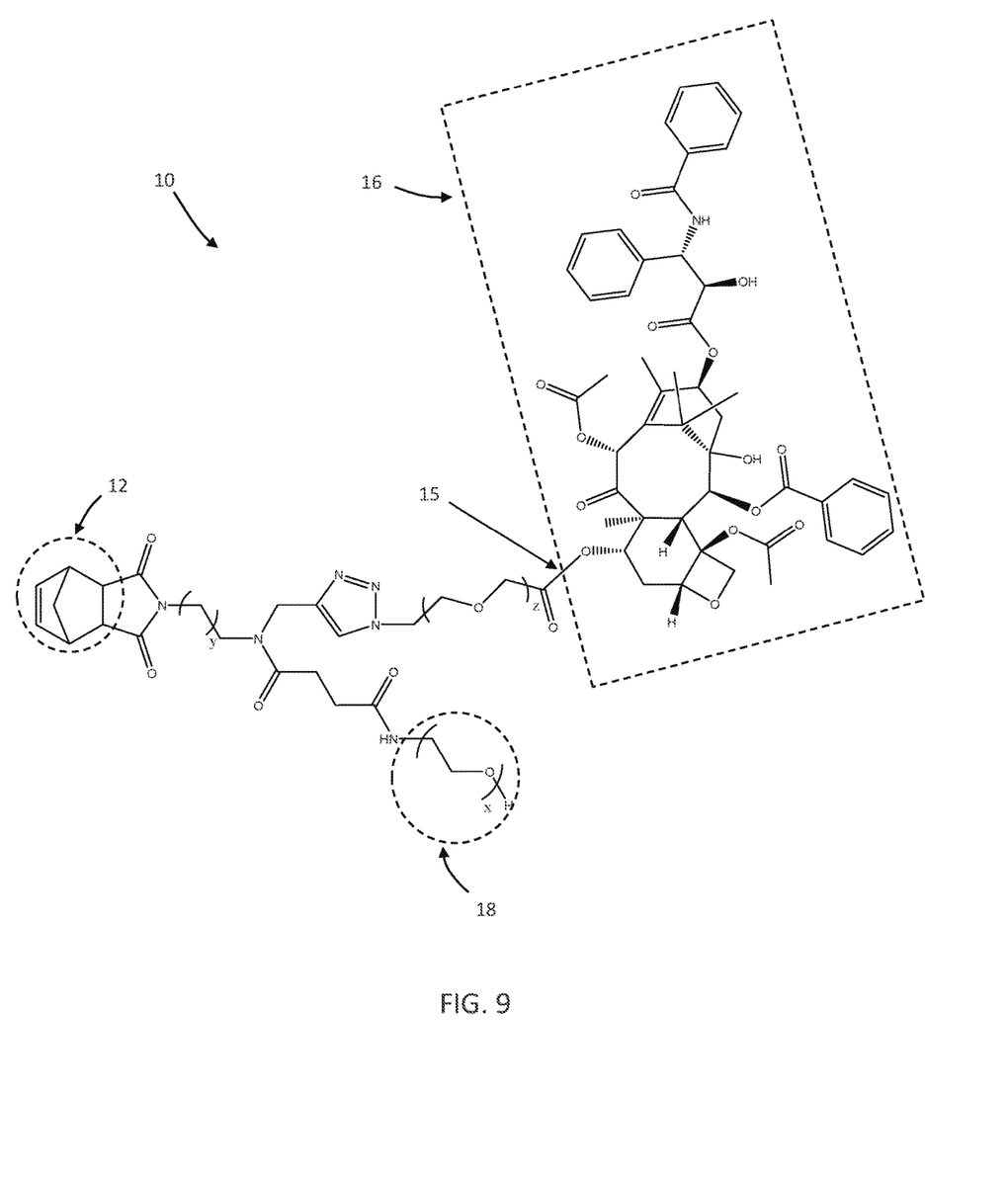
FIG. 9-10 are structures of macro-monomers that may be used to form brush-arm star polymers in accordance with various embodiments described herein.
Figure 10:
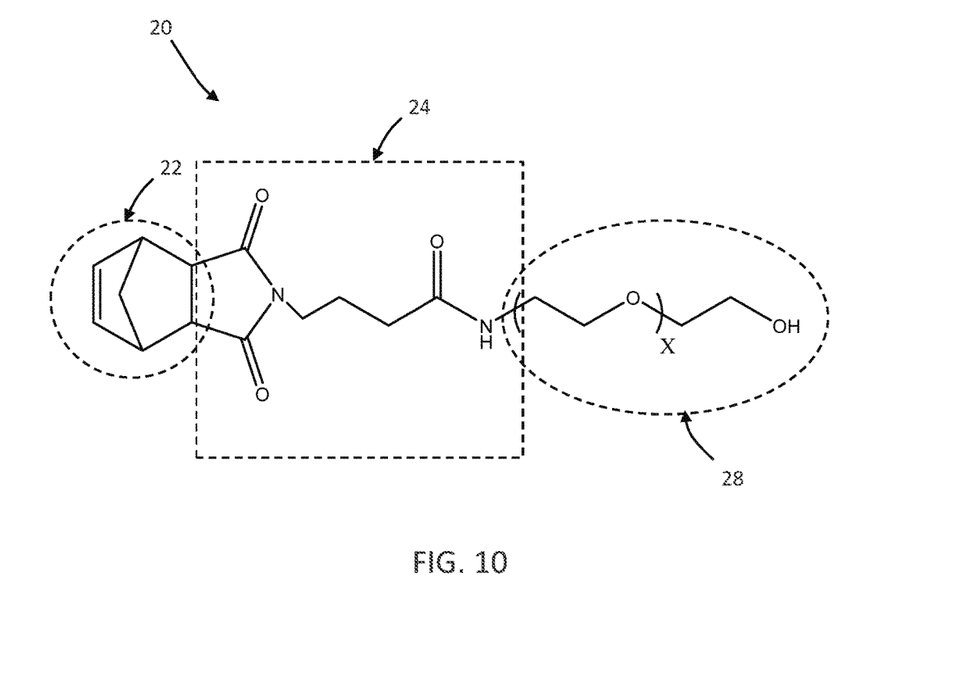
Figure 11:
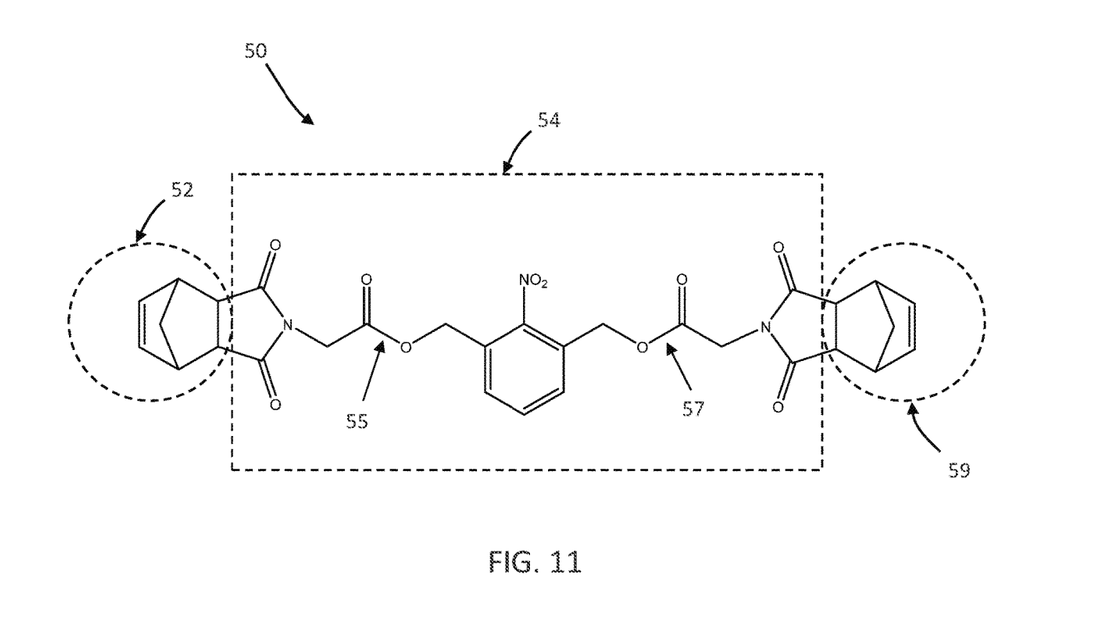
FIG. 11 is a structure of a cross-linker that may be used to form brush-arm star polymers in accordance with various embodiments described herein.

Some more specific examples of the macro-monomers 10, 20 and the cross-linkers 50 are shown in FIGS. 9-11. The macro-monomer 10 shown in FIG. 9 includes a norbornene monomer moiety 12 and a therapeutic agent 16, in this case paclitaxel, linked to the monomer moiety 12 via a cleavable linker. The linker may be cleaved at the indicated cleavage site 15 via hydrolysis to release the paclitaxel. The macro-monomer 10 also includes a polymer moiety 18, in this case PEG. For the macro-monomer 10 depicted in FIG. 9, x, y and z may be any suitable integer. For example, y may be an integer from 1 to 10, inclusive. In some embodiments, y is 6. Z may be an integer from 1 to 5, inclusive. In some embodiments, z is 3. X may be an integer from 30 to 100, inclusive. In some embodiments, x is 68. A macro-monomer 10 as depicted in FIG. 9 may be synthesized in any suitable manner. For example, the molecule may be synthesized as described in Liao et al., J. Am. Chem. Soc. 2014, 136, 5896-5899 in which paclitaxel is substituted for camptothecin, or may be synthesized in accordance with the teachings of U.S. Patent Application No. Publication 2016/0296631.

The macro-monomer 20 shown in FIG. 10 includes a norbornene monomer moiety 22 and a polymer 18, in this case PEG, linked to the monomer moiety 12 via a linker 24. For the macro-monomer 20 depicted in FIG. 10, x may be any suitable integer. X may be an integer from 30 to 100, inclusive. In some embodiments, x is 68. A macro-monomer 20 as depicted in FIG. 10 may be synthesized in any suitable manner. For example, the molecule may be synthesized as described in Liao et al., J. Am. Chem. Soc. 2014, 136, 5896-5899 or in U.S. Patent Application No. Publication 2016/0296631.

The cross-linker 50 shown in FIG. 11 includes first 52 and second 59 norbornene monomer moieties connected by the linker 54. The depicted linker 54 is a cleavable linker that may be cleaved at cleavage site 55 or 57 by hydrolysis. A cross-linker 50 as depicted in FIG. 11 may be synthesized in any suitable manner. For example, the molecule may be synthesized as described in Liao et al., J. Am. Chem. Soc. 2014, 136, 5896-5899 or in U.S. Patent Application Publication No. 2016/0296631.

In some embodiments, the macro-monomers 10 and 20 depicted in FIGS. 9-10 are polymerized via the norbornene moieties by ring-opening metathesis polymerization to produce bottle brush polymers having a living chain end and the bottle brush polymers are joined by the cross-linkers 50 depicted in FIG. 11 to produce a paclitaxel-containing brush-arm star polymer that may be coated on a medical device. The ratios of the macro-monomer 10, the macro-monomer 20, and the cross-linker 50 may be controlled to achieve desired release rates and timing. For example, higher cross-linker 50 proportions may delay or slow the release of paclitaxel relative to lower proportions of the cross-linker 50.

It will be understood that the compounds depicted in FIGS. 9-11 are merely for purposes of example and not limitation. Other suitable compounds that may be employed to produce suitable brush-arm star polymers are described in, for example, U.S. Patent Application Publication No. 2016/0296631.

The nanoparticles may comprise any suitable therapeutic agent. For purposes of the present disclosure, a diagnostic agent, such as a contrast agent or a dye, is a "therapeutic agent." A coating as described herein may include, for example, one or more of an anti-proliferative agent, an antibiotic, an anti-mitotic agent or the like. It will be understood and appreciated that some agents may have more than one therapeutic or diagnostic action. Preferably, a nanoparticle as described herein includes an anti-restenosis agent. For example, a coating may include one or more of paclitaxel, rapamycin, everolimus, zotarolimus, and the like.

Other examples of therapeutic agents that may be included in a nanoparticle for coating on an inflatable balloon are one or more of heparin or another thrombin inhibitor, hirudin, hirulog, argatroban, D-phenylalanyl-L-poly-L-arginyl chloromethyl ketone or another antithrombogenic agent, or mixtures thereof; urokinase, streptokinase, a tissue plasminogen activator, or another thrombolytic agent, or mixtures thereof; a fibrinolytic agent; a calcium channel blocker, a nitrate, nitric oxide, a nitric oxide promoter or another vasodilator; an antimicrobial agent or antibiotic; aspirin, ticlopdine or another antiplatelet agent; colchicine or another antimitotic, or another microtubule inhibitor; cytochalasin or another actin inhibitor; a remodeling inhibitor; deoxyribonucleic acid, an antisense nucleotide or another agent for molecular genetic intervention; GP IIb/IIIa, GP Ib-IX or another inhibitor or surface glycoprotein receptor; methotrexate or another antimetabolite or antiproliferative agent; an anticancer chemotherapeutic agent; dexamethasone, dexamethasone sodium phosphate, dexamethasone acetate or another dexamethasone derivative, or another anti-inflammatory steroid; dopamine, bromocriptine mesylate, pergolide mesylate or another dopamine agonist; a radiotherapeutic agent; a peptide, a protein, an enzyme, an extracellular matrix component, a cellular component or another biologic agent; captopril, enalapril or another angiotensin converting enzyme (ACE) inhibitor; alphatocopherol, superoxide dismutase, deferoxyamine, a 21-aminosteroid (lasaroid) or another free radical scavenger, iron chelator or antioxidant; and angiopeptin.

Unless content clearly dictates otherwise, general reference to a therapeutic agent in the present disclosure includes reference to salts of the agent, hydrates of the agent, polymorphs of the agent, isomers of the agent (including constitutional isomers and stereoisomers such as enantiomers and diasteriomers), and the like.

More than one therapeutic agent may be employed in the same or different nanoparticles to achieve release profiles as desired. In some embodiments, the same therapeutic agent is associated with different nanoparticles.

In some embodiments, one or more therapeutic agents that are not associated with a nanoparticle may be coated on a medical device. For example, any one or more of the therapeutic agents described above may be coated on the medical device. In some embodiments, a coating of a medical device comprises both paclitaxel and a paclitaxel-containing nanoparticle. The paclitaxel that is not associated with a nanoparticle may be available for immediate or near immediate release when contacted with tissue of a patient, while the paclitaxel associated with the nanoparticles may have a delayed or slower release rate.

The coating preferably comprises one or more therapeutic agents, whether associated with a nanoparticle or not, in a therapeutically effective amount. As used herein, "therapeutically effective amount" means an agent in an amount capable of inducing a therapeutic or preventive effect against the disease being treated or prevented. For example, if the disease being treated or prevented is restenosis of vascular tissue, the one or more agents present in the coating may be present in an amount effective to treat or prevent restenosis of the treated vascular tissue in the patient.

In some embodiments, the coating comprises one or more of zotarolimus, sirolimus, dexamethasone and paclitaxel.

Preferably, the coating comprises paclitaxel and is used to treat or prevent restenosis. In some embodiments, at least some or all of the paclitaxel is in anhydrous crystalline form. The coating provides for release and bioavailability of a therapeutically effective amount of paclitaxel when the coating contacts tissue at the site of intervention. Preferably, the coating provides for release from the medical device surface in periods of time less than 2 minutes, preferably between 30 seconds and 1 minute, and an absorption by the vascular tissue in periods of time ranging between 1 second and 25 minutes, preferably between 20 seconds and 25 minutes.

As used herein, "site of intervention" means the section of the blood vessel treated directly with a medical device described herein, and the adjacent portion in the tissues of which the post-procedure presence of paclitaxel can be detected. Generally, such section will extend up to 10 mm down- and upstream from the contact section with the coated medical device.

In some embodiments, a coating comprising paclitaxel that is not associated with a nanoparticle also comprises urea. The presence of urea in a paclitaxel-containing coating may promote the release of the paclitaxel. Paclitaxel may be dissolved in an appropriate solvent in the presence of urea and coated on the medical device, on another coating layer on the medical device, or mixed with other coating components and coated on the medical device. Urea may be present in any suitable amount, such as from 1 mg per mL to 100 mg per mL solvent. In some embodiments, a layer of paclitaxel and urea are coated directly on the medical device or are coated on another layer of the coating.

The coating may include any suitable number of layers. The therapeutic agent-containing nanoparticles and optional therapeutic agent not associated with a nanoparticle may be intermixed with other components of the coating and applied as a single layer. In some embodiments, a layer comprising therapeutic agent-containing nanoparticles is applied to the medical device and a layer, such as a polymeric layer, is applied on top of the nanoparticle-containing layer. In some embodiments, a layer, for example comprising a polymer, is applied to the medical device and a layer comprising the nanoparticles is applied on top of the previously applied layer.

In general, a coating layer may be disposed on the medical device or on a coating layer disposed on the medical device in any suitable manner. For example, a solution comprising the components of the layer, such as the nanoparticle or a therapeutic agent not associated with a nanoparticle, may be coated on the medical device by dipping the medical device in the solution, the solution may be sprayed on the medical device, or the solution may be deposited on the inflatable balloon with, for example, a syringe, micropipette, or other similar dispensing device.

If the medical device comprises, for example, an inflatable balloon or an expandable stent, the solution may be applied when the inflatable balloon is inflated or the stent is expanded, or when the balloon is in a folded condition or the sent is contracted. If the medical device comprises an inflatable balloon and the coating is applied when the inflatable balloon is in the folded condition, the solution may penetrate under the folds by capillary action or may be applied by, for example, micro-nozzles under the folds. It the medical device comprises a stent, the stent may be coated by filling the stent via capillary action as described in, for example, U.S. Patent Application Publication No. 2013/0284310 or may be coated in any other suitable manner.

One or more coatings of the solution may be applied to the medical device or other coating layer. The solvent may be allowed to evaporate under ambient conditions, under heated conditions, under vacuum drying, or heating and vacuum drying. The medical device or underlying coating layer may be fully or partially coated with the layer or subsequent layer.

The coatings described herein may be applied to any suitable medical device. Preferably, the medical device comprises a coated portion deliverable through a blood vessel of a patient. For example, the medical device may comprise an inflatable balloon or a stent, such as a self-expanding stent or a balloon expandable stent. The medical device may comprise a balloon catheter comprising an inflatable balloon.

Any suitable inflatable medical inflatable balloon may be coated with a nanoparticle coating described herein. The inflatable balloons may be compliant, semi-compliant or non-compliant. The inflatable balloons may be formed from any suitable material. For example, the inflatable balloons may be formed of polyamides, polyethylene terephathalate (PET), polyurethane, latex, silicone, polyethylene (PE), polypropylene (PP), polyetherimide (PEI), polytetrafluoroethylene (PTFE), ethylene tetrafluoroethylene (ETFE), fluorinated ethylene propylene (FEP), polyoxymethylene (POM), polybutylene terephthalate (PBT), polyether-block-ester, polyvinylchloride (PVC), polyether-block-amide, polyetheretherketone (PEEK), polyimide (PI), polyphenylene sulfide (PPS), polyphenylene oxide (PPO), poly(ethylene naphthalenedicarboxylate) (PEN), polysulfone, perfluoro(propyl vinyl ether) (PFA), or mixtures, combinations, copolymers thereof, and the like.

The inflatable balloon will typically have a length of at least 1 cm to 50 cm, preferably being in a range from about 1.5 cm to 20 cm, and may have inflated diameters in a range from 1.5 mm to about 20 mm, for instance 1.5 mm to 5 mm, but may be of any suitable size.

An inflatable balloon catheter comprising a coated inflatable balloon as described herein may be used for any suitable purpose. In preferred embodiments, the inflatable balloon catheter is an intravascular inflatable balloon catheter. For example, the inflatable balloon catheter may be an angioplasty catheter or a stent delivery catheter. Preferably, the inflatable balloon catheter is an angioplasty catheter. Preferably, the inflatable balloon catheter is used for treatment of restenosis in an artery.

In use, the inflatable balloon may be inflated by infusing fluid, such as water, saline or the like, into the inflatable balloon through, for example, a lumen of a catheter in communication with the interior surface of the inflatable balloon.

Any suitable implantable medical stent may be coated with a nanoparticle coating described herein. The sent may comprise a frame comprising one or more of a variety of biocompatible metals such as stainless steel, titanium, magnesium, aluminum, chromium, cobalt, nickel, gold, iron, iridium, chromium/titanium alloys, chromium/nickel alloys, chromium/cobalt alloys, such as MP35N and L605, cobalt/titanium alloys, nickel/titanium alloys, such as nitinol, platinum, and platinum-tungsten alloys. The metal composition gives the stent framework the mechanical strength to support the lumen wall of the vessel and sufficient longitudinal flexibility so that it can be transported through the cardiovascular system.

The stent may comprise a polymeric frame that may be biodegradable, biostable, or comprise a mixture of polymeric materials that are both biostable and biodegradable. Biodegradable polymers appropriate for the stents include polylactic acid, polyglycolic acid, and their copolymers, caproic acid, polyethylene glycol, polyanhydrides, polyacetates, polycaprolactones, poly(orthoesters), polyamides, polyurethanes and other suitable polymers. Biostable polymers appropriate for the stents include polyethylene, polypropylene, polymethyl methacrylate, polyesters, polyamides, polyurethanes, polytetrafluoroethylene (PTFE), polyvinyl alcohol, and other suitable polymers. These polymers may be used alone or in various combinations to give the stent unique properties such as controlled rates of degradation.

The stent frame may be formed by shaping a metallic wire or polymeric filament, or by laser cutting the stent from a metallic or polymeric sheet, or any other appropriate method. The surface of the stent framework may be cleaned by washing with surfactants to remove oils, mechanical polishing, electropolishing, etching with acid or base, or any other effective means to expose a clean, uniform surface that is ready for applying a coating.

The coating may include a polymer matrix comprising biodegradable polymers such as polylactic acid, polyglycolic acid, and their copolymers, caproic acid, polyethylene glycol, polyanhydrides, polyacetates, polycaprolactones, poly(orthoesters), polyamides, polyurethanes and other suitable polymers. The therapeutic agent-containing nanoparticles may be incorporated within the polymeric matrix, applied to the polymeric matrix, or the like. The coating may comprise one or more layer, such as described above.

The sent may be balloon-expandable or self-expanding. The coated stent may be positioned within a vessel through the use of a catheter to which the stent is coupled. The catheter may comprise an inflatable balloon that may be inflated to expand the stent such that the stent contacts a wall of the vessel, the balloon may be deflated, and the catheter removed leaving the stent in place. The catheter may include a sheath that retracts to enable expansion of a self-expanding stent to contact a wall of the vessel. When the sheath is fully retracted, the catheter may be removed from the vessel, leaving the stent in place.

Figure 12:
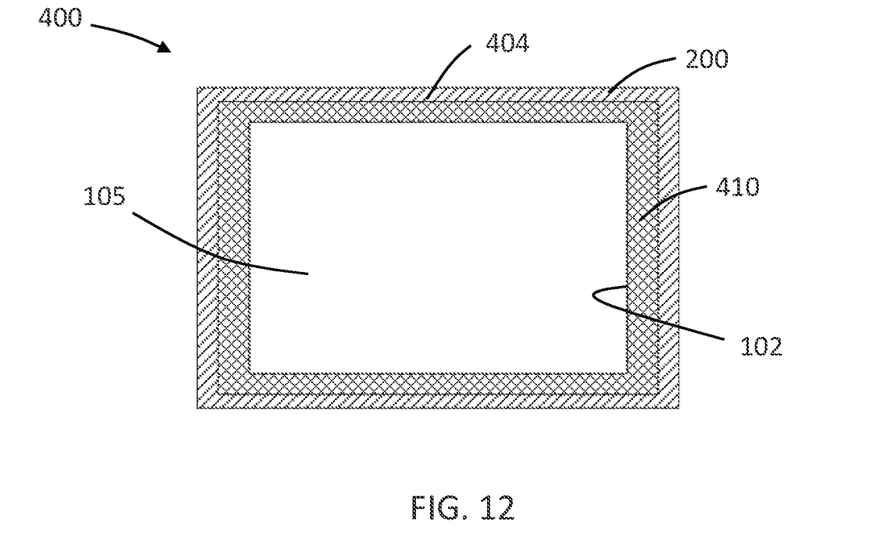
FIG. 12 is a schematic sectional view of an embodiment of a medical device having a coating comprising a nanoparticle for releasing a therapeutic agent.

Referring now to FIG. 12, a sectional view of a medical device 400 is shown. The medical device 400 comprises a body 410 having exterior surface 404. A coating 200 is disposed on the exterior surface 404 of the medical device 400. The coating 200 comprises a therapeutic agent-containing nanoparticle and may optionally comprise one or more polymers to assist in controlling the release of the nanoparticles or protecting the nanoparticles during the delivery process (such as navigating the device through the vasculature). The coating 200 may optionally comprise a therapeutic agent that is not associated with a nanoparticle. The coating 200 may comprise one or more additional layers (not shown). The body 410 may define an interior surface 102 defining an interior space 105. The device 400 may be or comprise an inflatable balloon or a stent.

Figure 13:
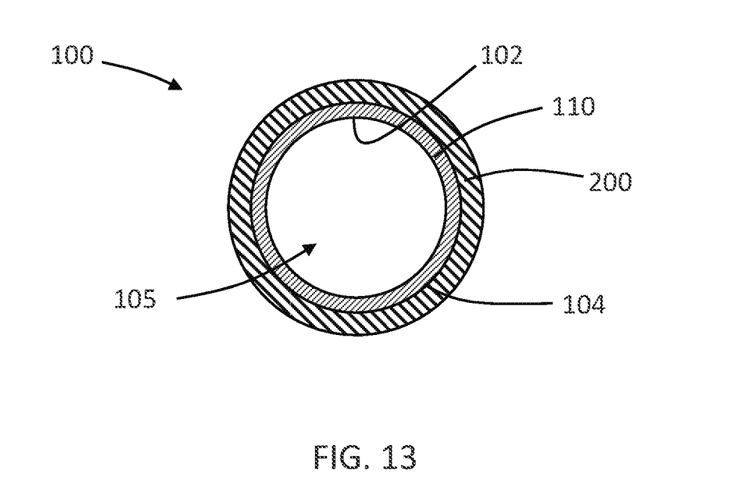
FIG. 13 is a schematic sectional view of an embodiment of an inflatable balloon having a coating comprising a nanoparticle for releasing a therapeutic agent.

Referring now to FIG. 13, a sectional view of an inflated inflatable balloon 100 is shown. The inflatable balloon 100 comprises a wall 110 defining an interior surface 102 and an exterior surface 104, the interior surface 104 defining an interior space 105. A coating 200 is disposed on the exterior surface 104 of the inflatable balloon 100. The coating 200 comprises a therapeutic agent-containing nanoparticle and may optionally comprise one or more polymers to assist in controlling the release of the nanoparticles or protecting the nanoparticles during the delivery process (such as navigating the balloon through the vasculature). The coating 200 may optionally comprise a therapeutic agent that is not associated with a nanoparticle. The coating 200 may comprise one or more additional layers (not shown).

Figure 14:
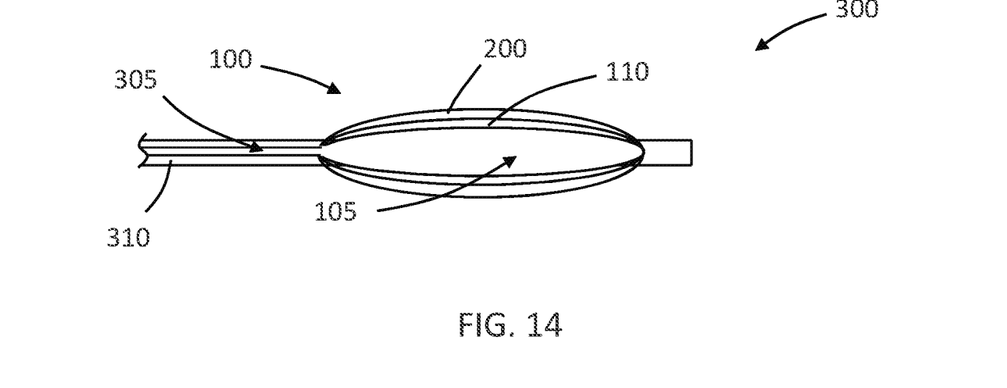
FIG. 14 is a schematic sectional view of an inflatable balloon catheter in accordance with various embodiments described herein.

Referring now to FIG. 14, a sectional view of an inflatable balloon catheter 300 is shown. The inflatable balloon catheter 300 includes a catheter 310 and an inflatable balloon 100 having a wall 110 defining an interior surface 102 and an exterior surface 104 (as shown in FIG. 13), the interior surface 102 defining an interior space 105. A coating 200, such as a coating described above regarding FIG. 13 is disposed on the exterior surface 104 defined by the inflatable balloon wall 110. The catheter 310 defines a lumen 305 in communication with the interior space 105 of the inflatable balloon 100 for inflating the inflatable balloon 100.

Figure 15A:
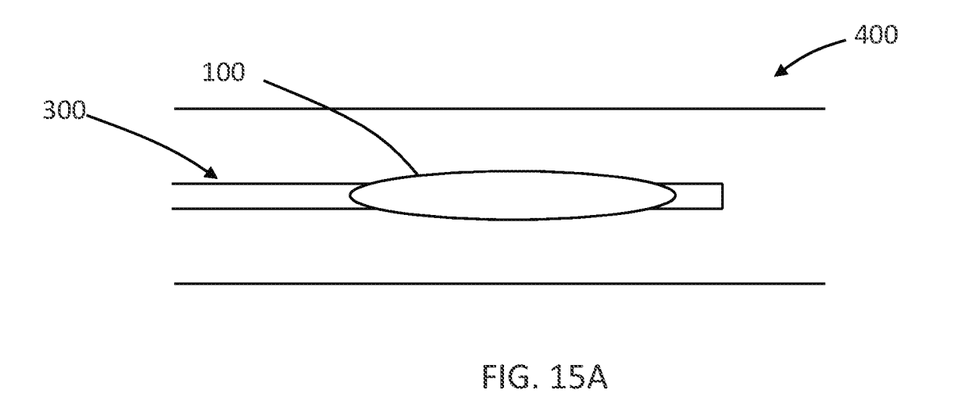
FIGS. 15A-B are schematic views of an inflatable balloon catheter in an artery in uninflated (FIG. 15A) and inflated (FIG. 15B) states in accordance with various embodiments described herein.
Figure 15B:
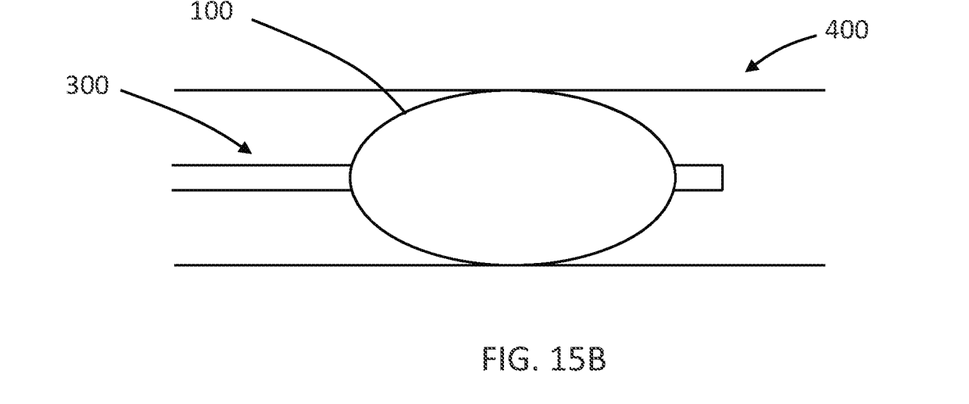

Referring now to FIGS. 15A-B, schematic drawings showing an inflatable balloon catheter 300 in a vessel 400 in uninflated (FIG. 15A) and inflated (FIG. 15B) states are shown. The inflatable balloon catheter 300 may be advanced within the vessel 400, such as an artery, until inflatable balloon 100 is aligned with a target site for intervention, such as a narrowing of the artery 400. The inflatable balloon 100 may be inflated (FIG. 15B) with fluid. Contact of the coating (not shown) disposed on the balloon with a wall of the artery 400 results in transfer of the coating 200 having the nanoparticles from the balloon 100 to the wall of the artery 400.

While described herein mainly in terms of treatment of restenosis in arteries, the balloon catheters described herein may be useful for treating other diseases in other passageways. For example, the balloon catheters described herein may be used in veins, coronary arteries, renal arteries, peripheral arteries including illiac arteries, arteries of the neck and cerebral arteries, and may also be advantageously employed in other body structures, including but not limited to arteries, veins, biliary ducts, urethras, fallopian tubes, bronchial tubes, the trachea, the esophagus and the prostate.

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. Thus, for example, reference to a "layer" includes examples having two or more such "layers" unless the context clearly indicates otherwise.

As used in this specification and the appended claims, the term "or" is generally employed in its sense including "and/or" unless the content clearly dictates otherwise. The term "and/or" means one or all of the listed elements or a combination of any two or more of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the inventive technology.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

As used herein, "providing" in the context of providing an article for use in a method means to make, purchase, or otherwise obtain the article.

It will be apparent to those skilled in the art that various modifications and variations can be made to the present inventive technology without departing from the spirit and scope of the disclosure. Since modifications, combinations, sub-combinations and variations of the disclosed embodiments incorporating the spirit and substance of the inventive technology may occur to persons skilled in the art, the inventive technology should be construed to include everything within the scope of the appended claims and their equivalents.

What is claimed is:

1. A medical device comprising:
a body having an exterior surface; and
a coating disposed on the exterior surface of the body, the coating comprising a therapeutic agent-containing nanoparticle, wherein the nanoparticle comprises a brush-arm star polymer, wherein the therapeutic agent of the therapeutic agent-nanoparticle comprises an anti-proliferative agent, and wherein the coating further comprises a second therapeutic agent that is not associated with the nanoparticle, wherein the second therapeutic agent is an anti-proliferative agent, wherein the therapeutic agent of the therapeutic agent-nanoparticle and the second therapeutic agent are the same,
wherein the coating is configured such that, upon implantation of the device at a target location or upon release of the coating from the device to tissue at the target location, substantial uptake of the second therapeutic agent occurs prior to substantial uptake of the therapeutic agent of the therapeutic agent-nanoparticle.

2. The medical device of claim 1, wherein the nanoparticle comprises a cleavable linker attaching the therapeutic agent to the nanoparticle.

3. The medical device of claim 2, wherein the cleavable linker is a linker cleavable by hydrolysis.

4. The medical device of claim 3, wherein the cleavage linker comprises an ester bond.

5. The medical device of claim 1, wherein the nanoparticle is formed by polymerization of one or more macromonomers, at least one of which comprises the therapeutic agent, to form bottle-brush polymers having a living chain end, and connecting the bottle-brush polymers having a living chain end with a cross-linker to form the brush-arm star polymer nanoparticle.

6. The medical device of claim 5, wherein the cross-linker comprises a cleavable linker.

7. The medical device of claim 6, wherein the cleavable linker is a linker cleavable by hydrolysis.

8. The medical device of claim 7, wherein the cleavage linker comprises an ester bond.

9. The medical device of claim 1, wherein the therapeutic agent is paclitaxel.

10. The medical device of claim 1, wherein the coating further comprises urea.

11. The medical device of claim 1, wherein the body comprises a stent.

12. The medical device of claim 1, wherein the body comprises an inflatable balloon defining an interior surface, wherein the interior surface defines an interior space.

13. The medical device of claim 12, further comprising a catheter comprising a lumen in fluid communication with the interior space of the inflatable balloon.

14. A method comprising:
providing a medical device according to claim 1;
inserting the medical device to the target location of a patient; and
contacting the medical device to tissue at the target location,
wherein contacting the medical device to the tissue causes the therapeutic agent-containing nanoparticle to be transferred to the tissue.

15. The method of claim 14, wherein the tissue of the patient to which the nanoparticle is transferred is a wall of an artery.

16. The method of claim 14, wherein the target location is a location of a narrowed artery.

17. The medical device of claim 1, wherein the coating further comprises a second therapeutic agent-containing nanoparticle comprising an anti-inflammatory steroid and a brush-arm star polymer.

18. The medical device of claim 9, wherein the coating further comprises a second therapeutic agent-containing nanoparticle comprising an anti-inflammatory steroid and a brush-arm star polymer.

19. The medical device of claim 18, wherein the anti-inflammatory steroid is dexamethasone, dexamethasone sodium phosphate, or dexamethasone acetate.

20. The medical device of claim 1, wherein substantial uptake of the therapeutic agent of the therapeutic agent-containing nanoparticle is delayed until the second therapeutic agent declines to approach tissue concentrations that are near an effective concentration of the therapeutic agent to maintain an effective concentration of the therapeutic agent in the target tissue for an extended time.

* * * * *